United States Patent
Dreyfuss

(10) Patent No.: US 7,442,202 B2
(45) Date of Patent: Oct. 28, 2008

(54) SUTURE ANCHOR ATTACHED TO TISSUE-FIXATION DISK WITHOUT TOP KNOT

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 915 days.

(21) Appl. No.: 10/644,779

(22) Filed: Aug. 21, 2003

(65) Prior Publication Data
US 2004/0039404 A1  Feb. 26, 2004

Related U.S. Application Data

(60) Provisional application No. 60/405,706, filed on Aug. 26, 2002.

(51) Int. Cl.
*A61B 17/04* (2006.01)
(52) U.S. Cl. ............................. 606/232; 606/300
(58) Field of Classification Search ............... 606/53, 606/72, 73, 232; 24/105, 362, 115 R–115 N
See application file for complete search history.

(56) References Cited

U.S. PATENT DOCUMENTS

| 4,632,100 A | 12/1986 | Somers et al. |
|---|---|---|
| 5,156,616 A | 10/1992 | Meadows et al. |
| 5,306,290 A * | 4/1994 | Martins et al. ............ 606/232 |
| 5,370,662 A | 12/1994 | Stone et al. |
| 5,630,824 A | 5/1997 | Hart |
| 5,665,112 A | 9/1997 | Thal |
| 5,720,765 A | 2/1998 | Thal |
| 6,027,523 A * | 2/2000 | Schmieding ............ 606/232 |
| 6,214,031 B1 | 4/2001 | Schmieding et al. |
| 6,267,766 B1 * | 7/2001 | Burkhart .................. 606/72 |
| 2002/0120292 A1 * | 8/2002 | Morgan .................. 606/232 |

* cited by examiner

*Primary Examiner*—Todd E. Manahan
*Assistant Examiner*—Timothy J Neal
(74) *Attorney, Agent, or Firm*—Dickstein Shapiro LLP

(57) ABSTRACT

A suture anchor attached to a tissue-fixation disk with at least one suture knot which resides in a recess in the suture anchor, rather than on the exposed surface of the tissue-fixation disk. The suture that connects the tissue-fixation disk to the suture anchor is looped through the tissue-fixation disk and through at least one suture passage formed through the proximal end of the suture anchor, the free ends of the suture being knotted together within the suture passage of the suture anchor.

17 Claims, 4 Drawing Sheets

SUTURE ANCHOR ATTACHED TO TISSUE-FIXATION DISK WITHOUT TOP KNOT

This application claims the benefit of U.S. Provisional Application Ser. No. 60/405,706, filed Aug. 26, 2002, the entire disclosure of which is incorporated by reference herein.

FIELD OF THE INVENTION

The present invention relates to suture anchors used for attachment of suture to bone, and more particularly, to a suture anchor equipped with a tissue fixation device but without a top knot.

BACKGROUND OF THE INVENTION

When soft tissue tears away from bone, reattachment becomes necessary. Various devices, including sutures alone, screws, staples, wedges, and plugs have been used to secure soft tissue to bone. Recently, various types of suture anchors have been developed for this purpose. For example, U.S. Pat. No. 4,632,100 discloses a cylindrical suture anchor which includes a drill bit at a leading end for boring a hole in a bone. The drill bit at the leading end is followed by a flight of threads for securing the anchor into the hole bored in the bone by the drill bit. Another example is U.S. Pat. No. 5,370,662 which discloses a self-tapping suture anchor having a flight of threads around a solid body. Similarly, U.S. Pat. No. 5,156,616 discloses a suture anchor having an axial opening for holding a knotted piece of suture.

The devices disclosed in the above-cited patents anchor suture to bone, but require the surgeon to tie a knot in the suture arthroscopically in order to achieve fixation of the soft tissue to the bone. As a result, devices which do not require arthroscopic knot tying for fixation have been proposed. For example, U.S. Pat. No. 6,027,523, the disclosure of which is incorporated by reference herein, describes a suture anchor equipped with a tissue-fixation disk which does not require arthroscopic knot tying for fixation. The free ends of suture of the suture anchor are secured to the tissue-fixation disk by using knots on the top of the tissue-fixation disk, as well as a drop of polyacrylamide or similar cement material to secure the knots to the tissue-fixation disk.

It would be desirable to provide a suture anchor with an attached tissue-fixation disk which does not require multiple suture knots that are exposed on the upper surface of the tissue-fixation disk.

SUMMARY OF THE INVENTION

The suture anchor of the present invention overcomes the disadvantages of the prior art and fulfills the needs noted above by providing a suture anchor attached to a tissue-fixation disk with a suture knot that resides in a recess in the suture anchor, rather than on the exposed surface of the tissue-fixation disk.

In the preferred embodiment of the present invention, the suture that connects the tissue-fixation disk to the suture anchor is a single strand which is looped through an eyelet or passage formed through the proximal end of the suture anchor and through the tissue-fixation disk. Advantageously, the free ends of the suture are tied in a knot within the eyelet of the suture anchor.

Other features and advantages of the present invention will become apparent from the following description of the invention which refers to the accompanying drawings.

DETAILED DESCRIPTION OF THE PREFERRED EMBODIMENTS

The present invention provides a suture anchor attached to a tissue-fixation disk with a suture knot that resides in a recess in the suture anchor, rather than on the exposed surface of the tissue-fixation disk. In the following preferred embodiment of the invention, the suture that connects the tissue-fixation disk to the suture anchor is a single strand which is looped through an eyelet formed through the proximal end of the suture anchor and through the tissue-fixation disk. Advantageously, the free ends of the suture are tied in a knot within the eyelet formed through the proximal end of the suture anchor.

Figure 1:
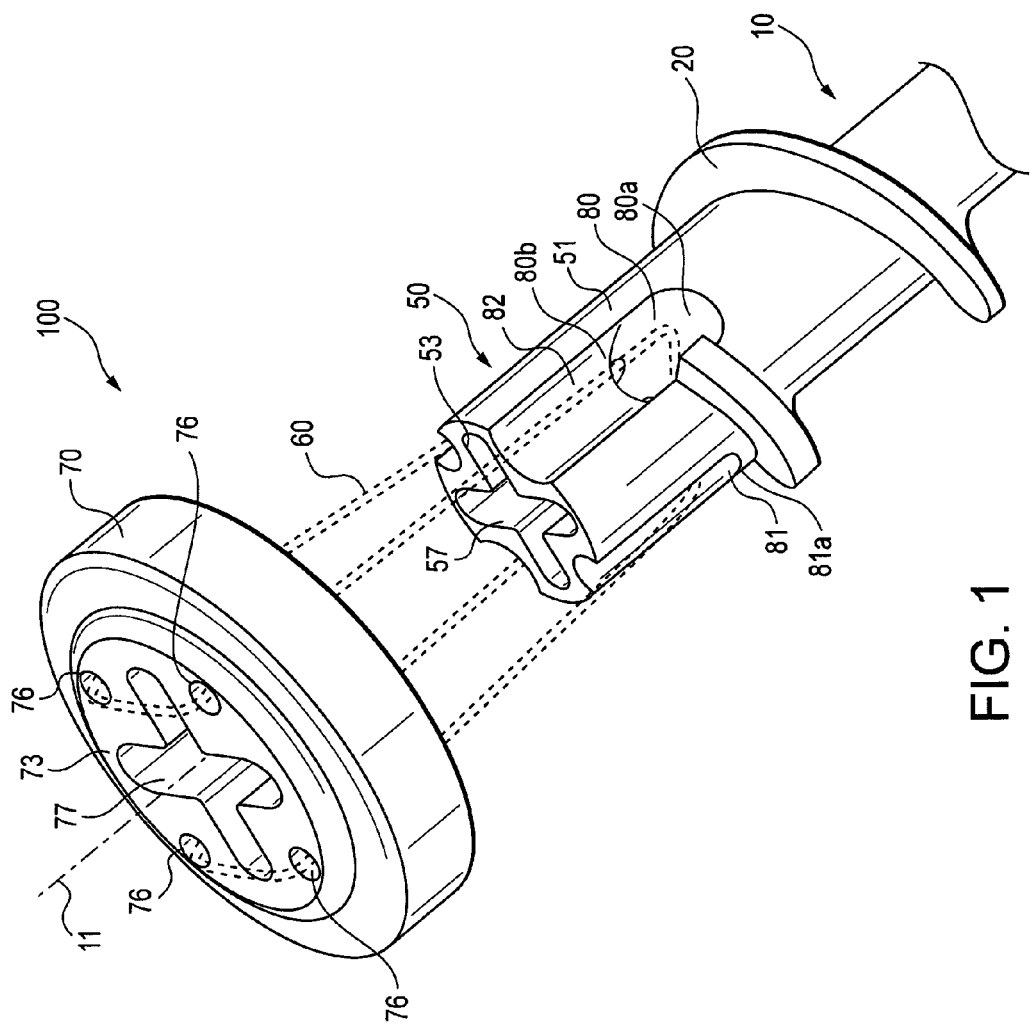
FIG. 1 illustrates a perspective diagrammatic view of a suture anchor in accordance with a first embodiment of the present invention.
Figure 3:
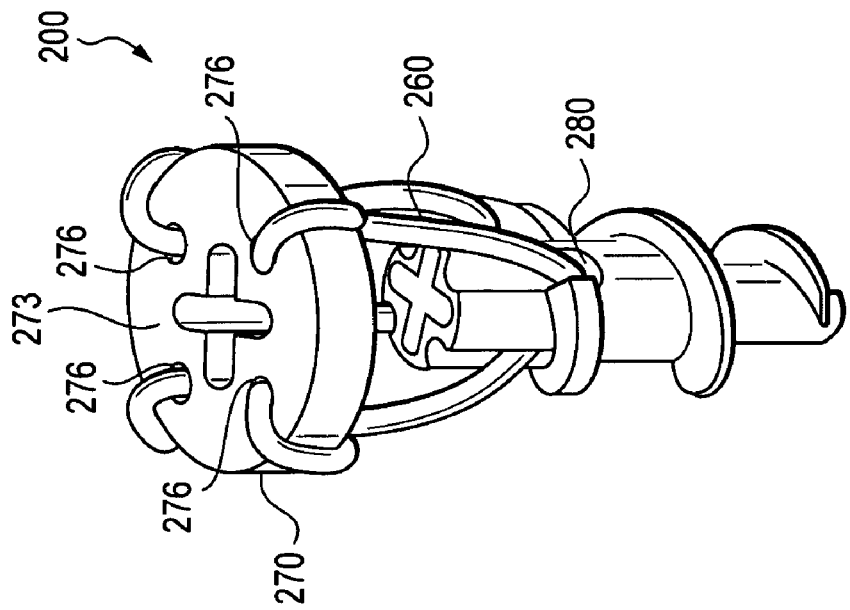
FIG. 3 illustrates a three-dimensional view of a suture anchor in accordance with a second embodiment of the present invention.
Figure 2:
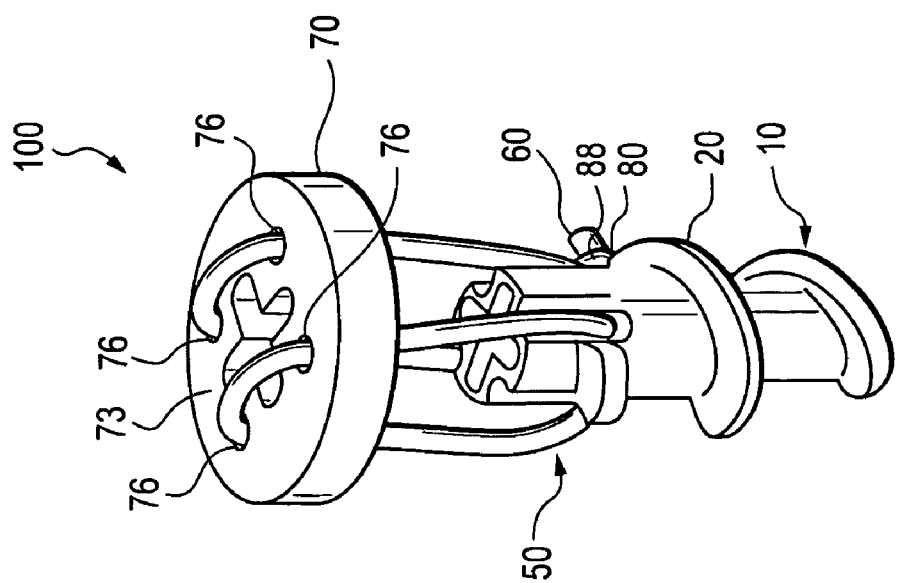
FIG. 2 illustrates a three-dimensional view of the suture anchor of FIG. 1.

Referring now to the drawings, where like elements are designated by like reference numerals, FIGS. 1-3 illustrate exemplary embodiments of suture anchors 100, 200 manufactured according to the present invention. As explained in more detail below, the suture anchor of the present invention does not require knots on the upper surface of the tissue-fixation disk.

The suture anchor 100 of FIGS. 1-2 comprises an elongated body member 10 and a driving end or head 50 which is associated with a tissue-fixation device 70. As shown in FIG. 1, the tissue-fixation device 70 is a disk. However, the invention also contemplates a tissue-fixation device of other geometric shapes and configurations, for example, a rod, a straight bar or a bended bar, among others. The elongated body member 10 has the shape of a tapered cylinder with a continuous thread 20 wrapping around the tapered cylinder in a clockwise direction. The elongated body member 10 is illustrated as having a particular configuration and geometry, that is, a corkscrew configuration such as the one disclosed and described in detail in U.S. Pat. No. 6,214,031 to Schmieding et al., the disclosure of which is incorporated by reference herein.

Extending from the proximal end of the elongated body member 10 of the suture anchor 100 is the driving end 50. As illustrated in FIG. 1, for example, the driving end 50 has a distal end 51 and a proximal end 53. The driving end 50 is provided with two transverse suture passages 80, 81, preferably both substantially perpendicular to longitudinal axis 11 of the elongated body member 10. The first transverse mounting suture passage 80 is seen in FIG. 1 to extend through the distal end 51 of the driving end 50 and to have opposed openings 80a, 80b. The second transverse mounting suture passage 81 is located proximal to the first suture passage 80, and is also provided with two opposed openings 81a, 81b. The second transverse mounting suture passage 81 is also preferably substantially perpendicular to the longitudinal axis 11 of the elongated body member 10, but may also be angulated if desired.

As also shown in FIG. 1, four grooves 82 are provided on either side of the driving end 50 and extend proximally from each of the openings of the transverse suture passages 80, 81. Grooves 82 accept and protect suture filament 60 as it passes along the sides of the driving end 50 of the suture anchor 100. As also illustrated in FIG. 1, cruciform drive socket 57 is formed in the proximal end 53 of the driving end 50. Preferably, the cruciform drive socket 57 is tapered inward distally and is provided to a depth that allows sufficient strength while not intersecting with suture passages 80, 81.

As further illustrated in FIG. 1, disk 70 is provided with cruciform driver opening 77 located centrally on the disk 70 and aligns with cruciform drive socket 57 of the driving end 50. Disk 70 is also provided with a pair of holes 76 through which a single suture strand 60 passes for capturing disk 70. As shown in FIG. 2, the ends of suture strand 60 are tied in a single knot 88 and the knot 88 is housed into a recess within one of the transverse suture passages 80, 81, rather than on top surface 73 of the disk 70. Alternatively, the ends of the suture strand 60 can terminate in the anchor separately, without being tied together in a single knot. In this latter embodiment, two separate knots are formed and housed within two separate suture passages or, alternatively, within a single suture passage.

FIG. 3 illustrates another embodiment of the present invention, in which a single suture strand 260 passes around the exterior of the disk 270 and through the holes 276. As in the previously-described embodiment, the filament 260 is tied in a single knot which is secured within eyelet 280 of the suture anchor 200, rather than on the upper surface of disk 270.

The suture anchor of the present invention may be typically employed in arthroscopic surgical procedures to repair a rotator cuff, for example, but may be also used in open surgical procedures. The suture anchor of the present invention has the advantage that it eliminates knotting on the upper surface of the tissue-fixation device improving the efficiency of attachment of soft tissue to bone in a surgical procedure.

Figure 4:
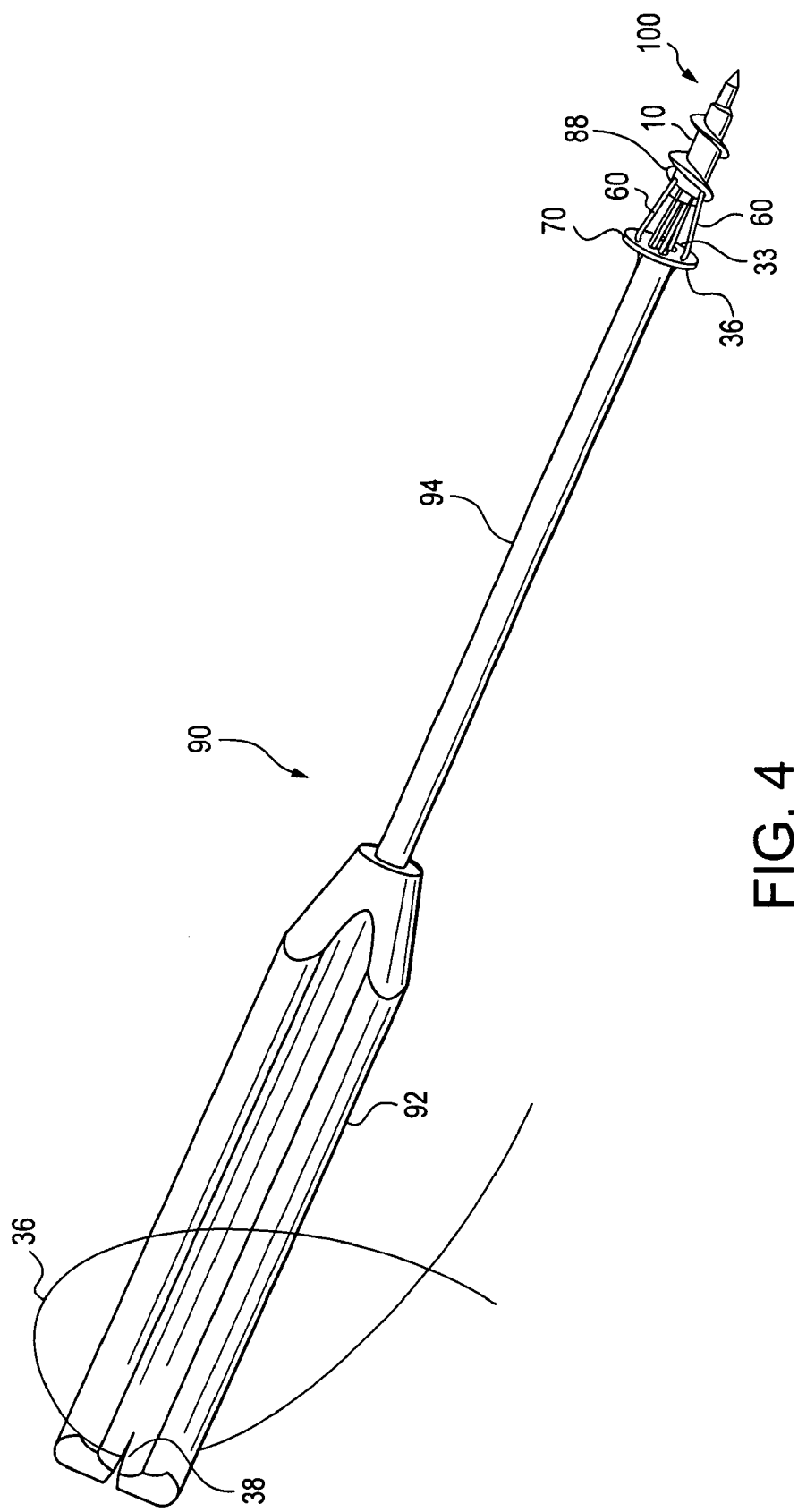
FIG. 4 illustrates a schematic perspective view of the suture anchor of FIG. 1 loaded on a driver of the present invention.
Figure 5:
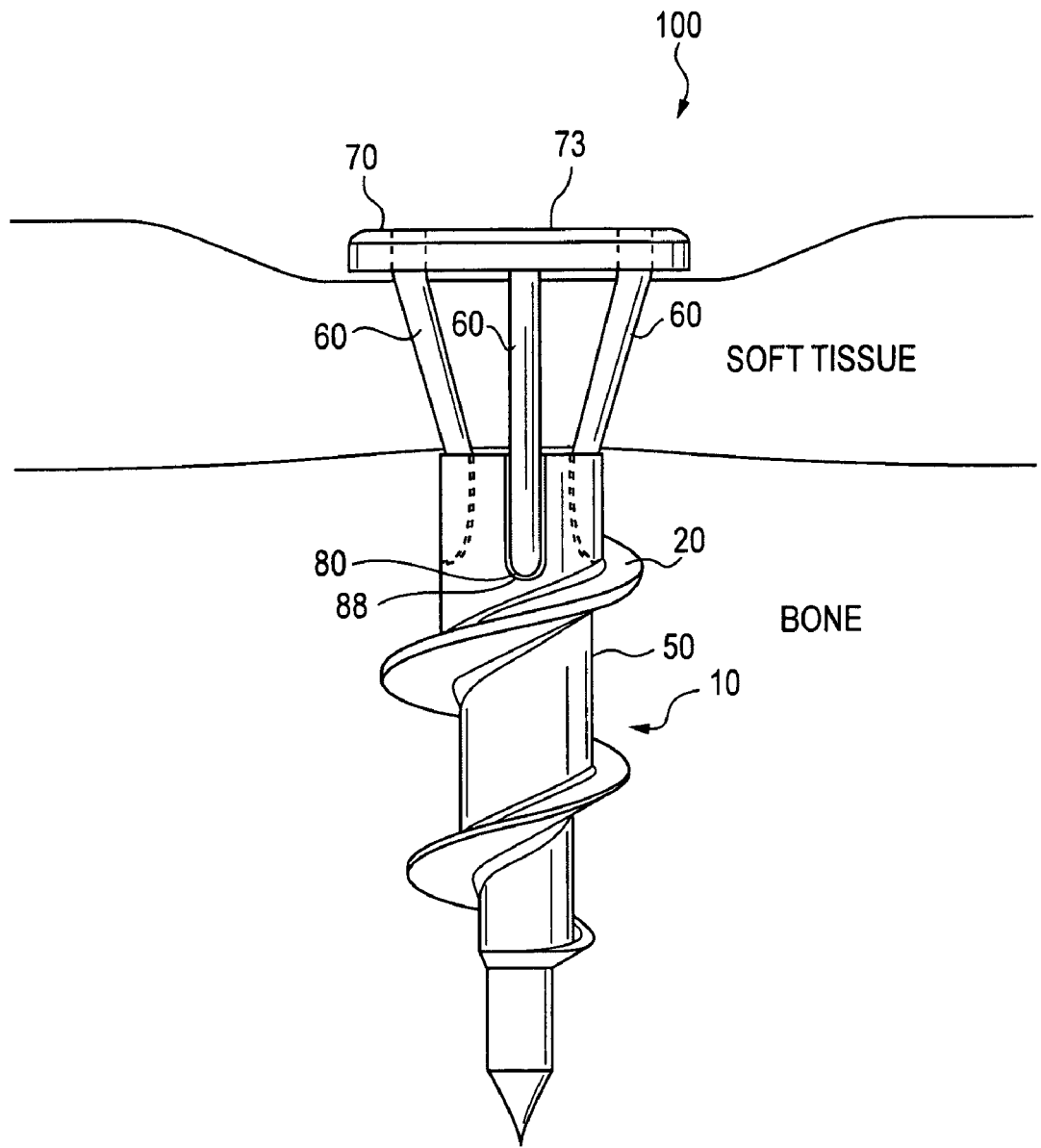
FIG. 5 illustrates a schematic elevation of the suture anchor of FIG. 1 which has been installed according to the present invention.

For example, FIG. 4 illustrates the suture anchor assembly 100 (FIGS. 1-2) according to the first embodiment of the present invention loaded on a driver 90 of the present invention, while FIG. 5 illustrates the suture anchor assembly 100 (FIGS. 1-2) installed in the body at a repair site so as to approximate soft tissue to bone. As shown in FIG. 4, driver 90 of the present invention has a cannulated handle 92 coupled to a cannulated driver shaft 94. The distal tip 95 of the driver 90 is shaped to matingly engage and complement both the cruciform drive socket 57 of the suture anchor 100 and the central opening 77 formed in the disk 70. Accordingly, driver 90 rotationally engages both the suture anchor 100 and the disk 70, such that the disk and the suture anchor turn simultaneously with the driver, avoiding tension on suture strand 60. Accordingly, no twisting or abrading of the suture strand 60 which captures the disk 70 occurs during insertion of the fixation device into bone.

As also shown in FIG. 4, cannulated driver 90 is provided with openings near the distal end which accept traction line 36. Traction line 36 is looped through holes 33 formed in disk 70, as illustrated in FIG. 4, and is passed through the cannulated driver 90. Tension on traction line 36 applied proximally holds the fixation device to the driver tip, the traction suture having been retained in notches 38 formed on proximal end of cannulated handle 92. Traction line 36 can also be used to confirm fixation strength after installation. Additionally, traction line 36 can be used to retrieve the disk 70 or the entire fixation device in the event of device failure during installation. Once the installation and fixation strength are determined to be adequate, traction line 36 easily is removed by pulling on one end of the traction line.

The driver 90 (FIG. 4) with the engaged suture anchor 100 of the present invention may be employed for installing the suture anchor in the body during an arthroscopic surgical procedure, such as rotator cuff repair. For example, FIG. 5 illustrates the suture anchor assembly 100 (FIGS. 1-2) installed in the body at a repair site so as to approximate soft tissue to bone, and after the removal of the driver 90 from the repair site. As illustrated diagrammatically in side elevation in FIG. 5, the suture anchor assembly 100 includes disk 70 which is provided with pair of holes 76 through which the single suture strand 60 passes for capturing disk 70. As shown in FIG. 5, the ends of suture strand 60 are tied in single knot 88 and the knot 88 is housed within one of the two suture passages 80, 81, rather than on top surface 73 of the disk 70.

The elongated body member 10 of the anchor 100, 200 of the present invention may be constructed from a conventional implantable biocompatible materials, such as titanium. The disk 70, 270 and suture strand 60, 260 may be manufactured from conventional biocompatible polymeric materials and may be absorbable or non-absorbable. A high strength suture sold by Arthrex, Inc., the assignee of the present application, under the tradename FiberWire and described in allowed U.S. Ser. No. 09/950,598, the disclosure of which is hereby incorporated herein by reference, may also be employed in the present invention.

Although the present invention has been described above with reference to a suture anchor having four grooves on the sides of the driving end, such as the suture anchor 100, 200 having four grooves 82 on the sides of the driving end 50, it must be understood that this embodiment is only illustrative and the invention is not limited to it. Accordingly, the present invention also contemplates a suture anchor having any plurality of grooves on the sides of the driving end, as long as the ends of the suture strand are tied in a knot which is housed within a recess of the driving end, and not on top of the tissue-fixation disk.

In addition, although the present invention has been described above with reference to a tissue-fixation device in the form of a disk, such as the tissue-fixation disk 70, 270, the invention also contemplates alternative embodiments accomplished with various types of tissue fixation means substituted for disk 70, 270, such as a ring, cross, straight bar, or bended bar, among others. In addition, various types of suture anchors, for example a smooth spike, barbed spike, cylindrical threaded anchor, or expanding anchor, can be used to anchor the assembly of the present invention.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A suture anchor assembly for attachment of tissue to bone, the suture anchor assembly comprising:

a suture anchor comprising a body member having a distal end, a proximal end, a longitudinal axis, an outer surface and two transverse suture passages extending through the body member, the suture passages being substantially perpendicular to the longitudinal axis, each of the suture passages having a respective suture recess provided therein;

a tissue-fixation device attached to the suture anchor, the tissue-fixation device having a plurality of holes; and a single suture strand that passes through the two transverse suture passages of the suture anchor and through the holes of the tissue-fixation device, the single suture strand attaching the suture anchor to the tissue-fixation device and terminating in at least one knot disposed within one of the suture recesses of the suture anchor.

2. The suture anchor assembly of claim 1 further comprising a plurality of suture grooves in the surface of the body member, such that a suture groove intersects each opening for the suture passage.

3. The suture anchor assembly of claim 1, wherein the tissue-fixation device is in the shape of a disk.

4. The suture anchor assembly of claim 1, wherein the body member comprises a plurality of thread flights extending from the outer surface of the body member.

5. A suture anchor assembly for attachment of tissue to bone, the suture anchor assembly comprising:

a suture anchor comprising a body member having a distal end, a proximal end, a longitudinal axis, an outer surface, a socket having a shape for receiving a suture anchor driver, and at least two transverse suture passages extending through the body member, the two suture passages being substantially perpendicular to the longitudinal axis, each of the suture passages being provided with a suture recess, wherein the suture recess is configured to house a suture knot;

a tissue-fixation device attached to the suture anchor, the tissue-fixation device being provided with a central aperture having a shape similar to the shape of the socket for receiving the suture anchor driver, the tissue-fixation device having a plurality of holes; and a single suture strand that passes through the two transverse suture passages of the suture anchor and through the holes of the tissue-fixation device, the single suture strand attaching the suture anchor to the tissue-fixation device and terminating in at least one knot disposed within one of the suture recesses of the suture anchor.

6. The suture anchor assembly of claim 5 further comprising a plurality of suture grooves in the surface of the body member, such that a suture groove intersects each opening for the suture passage.

7. The suture anchor assembly of claim 5, wherein the suture strand is looped slidingly through the suture passages.

8. The suture anchor assembly of claim 5, wherein the tissue-fixation device is in the shape of a disk.

9. The suture anchor assembly of claim 5, wherein the body member comprises a plurality of thread flights extending from the outer surface of the body member.

10. A method of attaching tissue to bone using a suture anchor assembly including a suture anchor having a body member, a distal end, a proximal end, a longitudinal axis, an outer surface and two transverse suture passages extending through the body member, the suture passages being substantially perpendicular to the longitudinal axis, each of the suture passages having a respective suture recess provided therein; a tissue-fixation device attached to the suture anchor, the tissue fixation device having a plurality of holes; and a single suture strand that passes through the two transverse suture passages of the suture anchor and through the holes of the tissue-fixation device, the single strand attaching the suture anchor to the tissue-fixation device and terminating in at least one knot disposed within one of the suture recesses of the suture anchor, the method comprising the steps of:

inserting the suture anchor assembly through the tissue;

coupling the suture anchor assembly to a driver;

applying tension to hold the suture anchor assembly to the driver; and installing the suture anchor assembly into bone, using the driver, to approximate the tissue to the bone.

11. The method of claim 10, wherein the suture anchor assembly further comprises at least one traction line extending proximally from the tissue-fixation device, the method comprising the further step of holding the suture anchor assembly onto the driver using the traction line.

12. The suture anchor assembly of claim 1 wherein the single suture strand passes continuously through the holes of the tissue-fixation device and back through the suture passages of the suture anchor, without terminating at the tissue-fixation device.

13. The suture anchor assembly of claim 12 wherein the single suture strand passes continuously through four holes of the tissue-fixation device and back through two suture passages in the suture anchor, forming two suture loops through the tissue-fixation device.

14. The suture anchor assembly of claim 12 wherein the single suture strand passes continuously through four holes of the tissue-fixation device and back through two suture passages in the suture anchor, forming four suture loops through the tissue-fixation device.

15. The suture anchor assembly of claim 5 wherein the single suture strand passes continuously through the holes of the tissue-fixation device and back through the suture passages of the suture anchor, without terminating at the tissue-fixation device.

16. The suture anchor assembly of claim 15 wherein the single suture strand passes continuously through four holes of the tissue-fixation device and back through two suture passages in the suture anchor, forming two suture loops through the tissue-fixation device.

17. The suture anchor assembly of claim 15 wherein the single suture strand passes continuously through four holes of the tissue-fixation device and back through two suture passages in the suture anchor, forming four suture loops through the tissue-fixation device.

\* \* \* \* \*